United States Patent [19]
Bennett et al.

[11] Patent Number: 4,749,503
[45] Date of Patent: Jun. 7, 1988

[54] METHOD AND COMPOSITION TO CONTROL MICROBIAL GROWTH IN METALWORKING FLUIDS

[75] Inventors: Edward O. Bennett; William D. Spoede, both of Houston, Tex.

[73] Assignee: Chemical Exchange Industries, Inc., Houston, Tex.

[21] Appl. No.: 837,492

[22] Filed: Mar. 7, 1986

[51] Int. Cl.$^4$ ............................................ C10M 173/02
[52] U.S. Cl. .................................. 252/49.3; 252/49.5; 252/52 R
[58] Field of Search ......................................... 252/49.3

[56] References Cited

U.S. PATENT DOCUMENTS

| | | | |
|---|---|---|---|
| 2,976,244 | 3/1961 | Bennett | 252/51.5 A |
| 3,106,533 | 10/1963 | Hallowell | 252/34.7 |
| 3,240,701 | 3/1966 | Furin | 252/8.55 |
| 3,280,029 | 10/1966 | Waldmann | 252/49.5 |
| 3,320,164 | 5/1967 | Brunel | 252/49.3 |
| 3,374,171 | 3/1968 | Davis | 252/34.7 |
| 3,442,805 | 5/1969 | Johnson | 252/34.7 |
| 3,515,671 | 6/1970 | Adams et al. | 252/54 |
| 3,531,411 | 9/1970 | Benson et al. | 252/32.5 |
| 3,630,898 | 12/1971 | Teeter et al. | 252/34.7 |
| 3,723,314 | 3/1973 | Davis | 252/33.4 |
| 3,791,975 | 2/1974 | Halkias | 252/49.5 |
| 3,799,876 | 3/1974 | White et al. | 252/51.5 R |
| 3,826,746 | 7/1974 | Schick et al. | 252/51.5 R |
| 3,859,221 | 1/1975 | Polk | 252/51.5 R |
| 3,951,833 | 4/1976 | Juda et al. | 252/51.5 R |
| 4,172,140 | 10/1979 | Shull et al. | 252/51.5 A |
| 4,435,297 | 3/1984 | Forsberg | 252/49.3 |
| 4,452,712 | 6/1984 | Laemmle | 252/49.3 |
| 4,469,611 | 9/1984 | Snyder, Jr. et al. | 252/49.3 |
| 4,493,780 | 1/1985 | Schwartz et al. | 252/49.3 |
| 4,533,481 | 8/1985 | Jahnke | 252/49.3 |
| 4,539,125 | 9/1985 | Sato | 252/49.3 |
| 4,552,678 | 11/1985 | Cargnino et al. | 252/49.3 |
| 4,563,294 | 1/1986 | Geymayer et al. | 252/49.3 |
| 4,564,461 | 1/1986 | Sköld et al. | 252/49.3 |

OTHER PUBLICATIONS

Schey, Tribology in Metalworking Friction, Lubrication and Wear, 1983, pp. 158–159.
Bennett, "Corrosion Inhibitors as Preservatives for Metalworking Fluids—Ethanolamines".

*Primary Examiner*—William R. Dixon, Jr.
*Assistant Examiner*—Ellen McAvoy
*Attorney, Agent, or Firm*—Arnold, White & Durkee

[57] ABSTRACT

A method for inhibiting microbial growth in aqueous fluid media, particularly media containing fatty oil or petroleum base components and modified metalworking fluids is described. The antimicrobial method involves adding an antimicrobially effective amount of n-hexyl ethanolamine to the aqueous fluid medium.

7 Claims, No Drawings

METHOD AND COMPOSITION TO CONTROL MICROBIAL GROWTH IN METALWORKING FLUIDS

BACKGROUND OF THE INVENTION

Antimicrobial compositions are generally added to various kinds of aqueous fluid media to reduce or inhibit the growth of microorganisms. In particular, a wide variety of industrial aqueous fluid media such as metalworking fluids used with metalworking equipment require antimicrobial compositions to control the growth microorganisms which eventually render the fluids rancid.

The development of high speed metal cutting and grinding has resulted in the creation of lubricants containing oils and chemicals stabilized in water. These fluids impart the cooling qualities of water and the lubricating properties of oil which prolong the life of cutting tools, reduce heat production, improve surface finish of the metal being machined, prevent warping and leave a rust-inhibiting film of oil on the worked piece.

Normally these fluids include fatty or petroleum oils, soaps, or synthetic based materials and additional additives such as antifoam agents, preservatives, coupling agents and rust inhibitors. The coolants are generally marketed in the form of concentrates which are normally diluted with water by the user in ratios of 1 part oil to about 20–40 parts of water, but these ratios may vary with particular operations. The lubricant is supplied to a machine from either an individual tank containing 50 to 100 gallons or from a large sump containing thousands of gallons which supplies many machines.

One of the problems often associated with such aqueous fluid media arises from the susceptibility of the media to the infestation and growth of various microorganisms such as bacteria and fungi (which particularly feed on the organic components thereof). The presence and buildup of such microorganisms can often lead to interference in the metalworking operations as a result of the clogging of filters, buildup of slime and sludge, development of odors, rust, emulsion instability, reduced tool life and poor finish. Furthermore, in machine shops where the workers' hands necessarily come in contact with the cutting oil, usually containing finely divided sharp metal cuttings, serious problems of dermatitis may arise. These and other such similar problems have resulted in the continuing need for better antimicrobial additives for aqueous fluid media such as metalworking fluids. Much effort has been devoted in recent years to controlling this problem; however, it continues to be a major annoyance which costs the metalworking industry many millions of dollars each year.

A number of suggestions have been made for inhibiting the growth of bacteria in aqueous fluids such as those described in U.S. Pat. Nos. 4,172,140, 3,951,830, 3,799,876, 3,515,671, and 2,976,244. The use of various formaldehyde preservatives for metalworking fluids including monomethylol dimethyl hydantoin and dimethylol dimethyl hydantoin has also been proposed (see Bennett, E. O., Int. Biodetn. Bull. 9: 95–100 (1973) and Maeda et al, Agr. Biol. Chem., 40: 1111–2222 (1976)).

Gray and Wilkinson in J. Gen. Microbiol., 39: 385–399 (1965) and J. App. Bact., 28: 153–164 (1965) describe the action of the ethylenediaminetetraacetic acid (EDTA) on some bacteria. The effectiveness of such chelating agents as EDTA along for bacterial control in aqueous systems is disputed as evidenced by U.S. Pat. Nos. 3,240,701, 3,408,843, and 3,591,679.

The antimicrobial compositions used in metalworking fluids seem to suffer from one or more disadvantages including high cost, unacceptable toxicity or low degree of effectiveness at the present state of the art.

Considerable advantages would result if a coolant could be formulated with an ingredient which has several different functions in regard to metalworking while, at the same time, exhibiting antimicrobial properties to provide partial or complete rancidity control. In this way, it might be possible to partially control increasing costs of these lubricants, as well as provide increased life under industrial conditions.

Antimicrobial agents and corrosion inhibitors constitute two important ingredients of metalworking fluids which commonly are depleted faster than the other components of the products. Quite often, both of these materials must be added to a coolant at periodic intervals in order to compensate for their loss from the coolants.

Preservatives are removed from the fluid as the chemicals combine with the microbes to bring about their inhibition or death. The greater the microbial population, the more cuickly they are lost from the system. Thus, the concentration of any preservative declines with time and may be reduced to subinhibitory levels in only a few weeks.

Rust inhibitors have an ability to absorb to metal surfaces. They usually coat the metal being worked, as well as the surfaces of the machine and circulation system. They sometimes even prevent the coating of metals with the oils commonly encountered in cutting fluids. Thus, the concentration of the rust inhibitor in a cutting fluid also declines with time as it is removed from the system on the metal parts being worked.

It would be worthwhile then to search for chemicals which can function both as corrosion inhibitors, as well as antimicrobial agents.

SUMMARY OF THE INVENTION

The present invention provides an antimicrobial composition useful for inhibiting the growth of microorganisms in an aqueous medium susceptible to microbial growth. The method involves adding to the aqueous medium an antimicrobially effective amount of n-hexyl ethanolamine. N-hexyl ethanolamine, when added to an aqueous fluid medium, provides an unexpected degree of preservation and antimicrobial activity over what one would expect from results obtained by using the chemically close structural antimicrobial ethanolamine agents, 2-(N-amyl) ethanolamine and 2-cyclohexyl ethanolamine.

DETAILED DESCRIPTION OF THE INVENTION

The antimicrobial composition of the present invention comprises an antimicrobially effective amount of n-hexyl ethanolamine as the active antimicrobial ingredient.

Preparation of N-hexyl Ethanolamine

This procedure outlines the steps involved in ethoxylating n-hexyl amine to n-hexyl ethanolamine and n-hexyl diethanolamine. A suitable reactor must have cooling water, a heat source of 350° F., and pressure rating of 100 psig. The material of construction may be carbon steel, stainless steel, or glass-lined steel.

The reactor was charged with various weights of n-hexyl amine for 100 pounds of reaction product. See CHART I showing analysis of crude product versus charge weights of n-hexyl amine and ethylene oxide. The maximum n-hexyl ethanolamine production occurs at approximately a ratio of 70% n-hexyl amine and 30% ethylene oxide. The typical industrial n-hexyl amine raw material specification is as follows:

| N—Hexyl Amine Raw Material Specification | |
|---|---|
| n-Hexyl Amines | 95.0% min. |
| Water | 0.2% max. |
| Imines | 0.2% max. |
| Other primary amines | 4.0% max. |
| Unknowns without primary amines | .6% max. |

CHART I
ETHOXYLATING n-HEXYLAMINE

| Molar Ratio of Reactants | | CHARGE PER 100 lbs. of Reactant | | Analysis of Crude Product | | | | | | | |
|---|---|---|---|---|---|---|---|---|---|---|---|
| | | | | NHA | | NHEA | | NHDEA | | Heavies | |
| NHA | EO | lbs. NHA | lbs. EO | Wt % | Mole % | Wt % | Mole % | Wt % | Mole % | Wt % | Mole % |
| 1 | 0.602 | 79.2 | 20.8 | 48 | 60 | 29 | 26 | 21 | 14 | — | — |
| 1 | 1.004 | 69.6 | 30.4 | 30 | 42 | 34 | 33 | 33 | 25 | — | — |
| 1 | 1.406 | 62.0 | 38.0 | 22 | 33 | 29 | 30 | 47 | 37 | — | — |
| 1 | 1.900 | 54.7 | 45.3 | 3.2 | 5.8 | 9.1 | 11.4 | 85.6 | 82.8 | — | — |
| 1 | 2.02 | 53.2 | 46.8 | 0.1 | 0.2 | 0.4 | .5 | 90.6 | 93.9 | 6.4 | 5.4 |

Note: Weight and Mole % were based on uncorrected area % from GC data. As a result, NHEA and NHDEA are slightly understated. Response factors will be published later.

The reactor was pressured to 30 psig with nitrogen, then vented to 0 psig. This pressuring and venting cycle was repeated five times to remove all oxygen. Thereafter, the reactor vent was closed.

The n-hexyl amine was heated to 265° F., plus or minus 5° F. The pressure increased slightly to above atmospheric (about 15 psig). Next, ethylene oxide was added to the reactor. The reaction proceeded exothermicly to 310° F., plus or minus 5° F., at which point cooling was begun. (More than five percent of the ethylene oxide charge should not be added before the cooling procedure is begun.) The temperature of the reaction was controlled at 320° F., plus or minus 5° F., by the rate of ethylene oxide addition. The pressure was noted as between 30-60 psig. At the end of ethylene oxide addition, the temperature held at 320° F., plus or minus 5° F., for one hour.

Next, the reactor was cooled to below 150° F. The product was discharged to storage and the color protected with a nitrogen pad.

N-Hexyl Ethanolamine Purification

This procedure outlines the separation of n-hexyl ethanolamine from the crude reaction products of n-hexyl amine and ethylene oxide by distillation. The major components in feed to distillation included: water, n-hexyl amine, unknown lights, n-hexyl ethanolamine, n-hexyl diethanolamine, and heavy ethoxylated amines.

Crude reaction product was charged to a distillation unit. For ease of operation, suitable apparatus should contain at least ten theoretical trays. The product was protected with nitrogen; thereafter, a vacuum was pulled to 90 mmHg in an overhead condenser. Heating was begun at a reflux ratio of 1:1. The water, unknown lights, and free amines were removed. The vapor temperature in the overhead condenser was between 150°-160° F. The water came overhead at 150° F. and the amine at 160° F. The bottoms temperature remained below 350° F. to prevent cracking.

The boiling point difference between n-hexyl amine and n-hexyl ethanolamine is at least 200° F. at reduced pressures. Essentially, complete removal of the amine was indicated by a quick temperature rise from 160° F. to 200° F. in the overhead condenser.

When the overhead temperature rose to about 200° F., the batch pot composition was confirmed by gas chromatography. The ratio of n-hexyl amine to n-hexyl ethanolamine was less than 0.004. The water content was less than 0.1% by Karl Fisher.

After the n-hexyl amine was removed from the batch pot, heating was stopped and the pressure reduced to 50 mmHg. After pressure reached 50 mmHg, the heating began to 302° F., plus or minus 5° F., and reflux maintained at 1:1 ratio. N-hexyl ethanolamine was removed overhead as a product and protected with nitrogen, then analyzed by gas chromatography.

| N—HEXYLETHANOLAMINE C.A.S. REGISTRY NO. 54596-69-9 | |
|---|---|
| Specifications | |
| N—Hexylethanolamine | 98.0% min. by weight |
| Water | 0 5% max. |
| Color | 50 APHA max. |
| Appearance | Clear liquid, free of suspended matter. |
| Typical Analysis | |
| Properties | Value |
| Boiling Point (at 20 mm Hg.) | 133° C. |
| Molecular Weight | 145 |
| Composition | |
| Total Hexyl Ethanolamine | 98.5% |
| N—n-Hexyl ethanolamine | 94-97% |
| Other C$_6$ ethanolamines | 3-8% |
| Water | 0.2% |
| n-Hexylamine | 0.2-0.4% |
| Volatiles | 0.1-0.2% |
| Hexyl diethanolamine and heavier ethoxylates | 0.8-1.0% |

Alternate N-Hexyl Ethanolamine Synthesis Scheme

In an alternate synthesis scheme for n-hexyl ethanolamine, the ethoxylation steps remained the same as above in sequence, temperature and pressure. However, the preferred weight fraction of n-hexyl amine to ethylene oxide was lowered to approximately 88 pounds n-hexyl amine to 12 pounds ethylene oxide to yield 100 pounds of reaction mass. The weight ratio of mono to di ethoxylates in the reaction mass was approximately 4.0–4.2 mono to 1.0 di. The purification section was also the same except the process was stopped after removal of n-hexyl amine overhead. The final bottoms fraction contained n-hexyl ethanolamine and some diethoxylates byproducts (less than 20% by weight).

Antimicrobial Compositions

In use, the n-hexyl ethanolamine antimicrobial composition is added to an aqueous fluid medium as a solution.

In order to achieve practical level of inhibition of microorganism growth in the aqueous fluid medium, it is necessary to include therein the n-hexyl ethanolamine in an amount sufficient to inhibit the growth of microorganisms. As used herein, the term "antimicrobial amount" is to be understood as that amount of n-hexyl ethanolamine which, when added to an aqueous fluid medium, will acceptably inhibit the growth of microorganisms in the use of said medium.

Generally at least 1000 parts of the n-hexyl ethanolamine are added per million parts of the aqueous fluid medium. Amounts ranging from about 1000–4000 parts by weight of n-hexyl ethanolamine per million parts by weight of the aqueous fluid medium provides effective antimicrobial activity.

As used herein, the term "aqueous fluid medium" is meant to encompass water, oil in water, water in oil emulsions (including concentrates) and like compositions susceptible to the infestation and growth of microorganisms. Thus, for instance, metalworking fluids or cutting oil fluids (in diluted as well as undiluted form), together with conventional additives such as corrosion inhibitors, etc., are included.

The antimicrobial compositions may be added directly to undiluted metalworking fluids. As used herein, the term "metalworking fluid" is intended to encompass those compositions known in the art as "metal cutting fluids", "cutting fluids", "coolants", "lubricants", "rolling oils", "drawing fluids", "mold release fluids", "grinding fluids" and like products used in the processinc of metals as described more fully by Springborn, R. K. "Cutting and Grinding Fluids": Selection and Application, ASTME (1967) and Wilbert J. Olds, "Lubricants, Cutting Fluids and Coolants", Cahner's Books, the entire contents of each being incorporated herein by reference. Emulsifiable or water miscible oils are widely used in the industry. Mixed with water, they form emulsions for use in rolling, drawing, machining and grinding where the need is for both cooling and lubrication. More recently, water miscible fluids using less oil (or no oils) and based on chemicals with or without surface active agents, have provided industry with products of even greater heat conducting properties for still higher machining rates.

The following examples are offered in order to more fully illustrate the invention, but are not to be construed as limiting the scope thereof.

Experimental Procedures

The test units consisted of quart jars placed in rows. Above each row, a metal framework was constructed to support the aeration system which consisted of aquarium valves connected together with plastic tubing. The amount of aeration of each unit was controlled by adjusting the valves. Capillary pipettes were employed as aerators to produce a fine steam of bubbles in the diluted coolants.

Five hundred ml of tap water (120 ppm hardness) was added to each jar. The n-hexyl ethanolamine was added to each jar along with 15.0 ml of coolant concentrate to produce the desired coolant concentration. Each unit was then made up to a total volume of 600.0 ml by adding additional tap water.

Each test unit was inoculated with a mixture of bacteria and fungi which were obtained and maintained as described in Bennett, "The Deterioration of Metal Cutting Fluids", *Prog. Indust. Microbiol.* 13: 121–249 (1974), the entire contents of which are incorporated herein by reference. Each unit was inoculated once each week with 1.0 ml of a 50-50 mixture of both inocula.

Each unit was examined once each week for its microbial content for as long as the count remained below 100,000 organisms/ml. Two consecutive counts in excess of this figure at weekly intervals was considered to constitute a failure and the test was discontinued at that time. In addition, all units which contained less than 100,000 organisms/ml were studied for a 182-day test period and discarded at that time.

Two different types of control experiments were included. Each shipment of fresh coolant was tested upon arrival to determine if the product exhibited any inhibitory properties, as defined in the previous paragraph. All of the coolants used in the investigation were especially prepared by coolant manufacturers for this work and they did not contain a preservative. None of the products employed in this investation exhibited any inhibitory properties and failed in the first week of testing. The second set of controls consisted of a particular cutting fluid preserved with a commonly used cutting fluid preservative. Normally, these control units fail in 21 to 28 days due to mold growth and have done so for the past several years. The controls functioned normally during the test period.

Since the test units were under constant aeration, there was considerable evaporation from each unit. The units were calibrated at the 600.0 ml mark and, once or twice each week, depending upon environmental conditions, distilled water was added to each unit to bring the liquid level back to this mark. Distilled water was used in order to avoid a buildup of inorganic salts in the test units.

Results

A series of sample jars were prepared according to the procedure outlined above to ascertain the antimicrobial effects of n-hexyl ethanolamine made according to the alternate synthesis scheme described above. The sample coolants were mixed with water in a ratio of 1:40 (coolant to water). The results are set forth in CHART II below, wherein the time in days is recorded when the count in such test reached the level of 100,000 or the test discontinued.

CHART II
ANTIMICROBIAL EFFECTIVENESS OF
N—HEXYL ETHANOLAMINE IN CUTTING FLUIDS

| PRODUCT | CONCENTRATION (PPM) OF N—HEXYL ETHANOLAMINE | DAYS OF TESTING BEFORE COUNTS EXCEEDED 100,000 ORGANISMS/ML |
|---|---|---|
| 1. Anderson Lusol | 1500 | 28 |
|  | 2500 | 114 |
| 2. Anderson Shamrock | 2500 | 14 |

CHART II
ANTIMICROBIAL EFFECTIVENESS OF
N—HEXYL ETHANOLAMINE IN CUTTING FLUIDS

| | PRODUCT | CONCENTRATION (PPM) OF N—HEXYL ETHANOLAMINE | DAYS OF TESTING BEFORE COUNTS EXCEEDED 100,000 ORGANISMS/ML |
|---|---|---|---|
| 3. | Applied Chemicals 1-14 | 2500 | 70 |
| 4. | Ashland Adcool 2 | 1500 | 0 |
| | | 2000 | 182* |
| 5. | Ashland Adsol 3 | 2500 | 182* |
| 6. | Baum's Macson 435 | 2500 | 182* |
| 7. | Baum's ProSol K-42 | 2500 | 182* |
| 8. | Berocut 8501 | 2500 | 70 |
| 9. | Berocut 8503 | 2500 | 182* |
| 10. | Buckeye | 2000 | 365* |
| 11. | Castrol 7100 | 2500 | 56 |
| 12. | Celanese 2J20 | 2500 | 182* |
| 13. | Chemtool 174 | 2000 | 14 |
| 14. | Chemtool 250 | 1500 | 14 |
| | | 2500 | 161 |
| 15. | Chemtrend CT-540 | 1500 | 98 |
| 16. | Cimcool Five Star | 2500 | 182* |
| 17. | Cimcool (H) | 2500 | 56 |
| 18. | Conoco OS 547L | 2500 | Sample lost at 49 days |
| 19. | Cook Coolex 40 | 2500 | 182* |
| 20. | Dober Lub A | 2500 | 63 |
| 21. | Dober Lube B | 1500 | 0 |
| | | 2000 | 14 |
| 22. | Emory 2885 | 2000 | 98 |
| 23. | Emory 2885-A | 2000 | 28 |
| 24. | Etna Master Draw A | 2500 | 63 |
| 25. | Etna Master Draw B | 2500 | 49 |
| 26. | Exxon Kutwell 40 | 1500 | 0 |
| | | 2500 | 56 |
| 27. | Exxon Kutwell 240 | 2500 | 182* |
| 28. | Gulfcut H.D. | 2500 | 182* |
| 29. | Hodson EZ Cool 850 | 2500 | 182* |
| 30. | Houghton 1133-41 | 2500 | 161 |
| 31. | IRMCO emulsion | 2000 | 245 |
| 32. | IRMCO 103 | 2500 | 182* |
| 33. | Ironsides | 2000 | 182* |
| 34. | Ironsides 381 | 2500 | 98 |
| 35. | Ironsides 379 | 2500 | 182* |
| 36. | S. C. Johnson 5113 | 1500 | 70 |
| 37. | Larson PL 95K | 2500 | 182* |
| 38. | S. H. Mack PTL 4184 | 1500 | 0 |
| | | 2000 | 112 |
| 39. | Master Trim Regular | 2500 | 182* |
| 40. | Mobil P-174 | 1500 | 91 |
| | | 2000 | 112 |
| 41. | Mobil Emulsilube | 2500 | 182* |
| 42. | Monroe Primecut (Old) | 2500 | 365* |
| 43. | Monroe Primecut (New) | 2500 | 182* |
| 44. | Monroe Choice Cut | 2500 | 182* |
| 45. | Nalco XL174-L | 2500 | 49 |
| 46. | Oil Craft | 1500 | 0 |
| | | 2500 | 14 |
| 47. | Petron 54-4 | 1500 | 0 |
| 48. | Petron II 54-4 | 2500 | 182* |
| 49. | Petron K₃-4 | 2500 | 182* |
| 50. | Polar Chip | 2500 | 182* |
| 51. | Process Research Products | 2500 | 91 |
| 52. | Quaker coolant | 1500 | 0 |
| | | 2000 | 182* |
| 53. | Rust Lick Alucut WS | 2500 | 182* |
| 54. | Rusk Lick 600B | 2500 | 42 |
| 55. | Sanson emulsion | 2500 | 182* |
| 56. | Shell Dromus B | 1500 | 0 |
| 57. | Shell DM soluble 2500 | 2500 | 42 |
| 58. | Sintolin E | 2500 | 14 |
| 59. | Sintolin S | 2500 | 182* |
| 60. | D. A. Stuart emulsion | 2000 | 245 |
| 61. | Sun Seco | 2500 | 182* |
| 62. | Tapmatic Molecular Edge II | 2500 | 182* |
| 63. | TCI 4800 | 2500 | 182* |
| 64. | TCI 3900 | 2500 | 182* |
| 65. | Tower A-1344 | 2500 | 161 |
| 66. | Tower W-2122 | 2500 | 182* |
| 67. | Union 501 | 1500 | 0 |
| | | 2500 | 42 |
| 68. | Union Soluble 10 | 2500 | 182* |
| 69. | Vantrol | 2000 | 365* |
| 70. | Vasu soluble | 2500 | 21 |
| 71. | White & Bagley X-5864 | 2500 | 182* |
| 72. | Yusiro A | 2500 | 182* |
| 73. | Yusiro B | 2500 | 182* |

*Still inhibitory when taken off test or at time of report.

Test failures in less than 60 days or less were considered unacceptable from the standpoint of potential industrial and commercial applications.

On reviewing previous experiments of tested ethanolamines, the presently tested n-hexyl ethanolamine exhibited unexpectedly high antimicrobial activity as compared to the chemically close structurally related compounds: 2-(N-amyl) ethanolamine and 2-cyclohexyl ethanolamine. The antimicrobial test results of several ethanolamine compositions have previously been reported in Bennett, "Corrosion Inhibitors as Preservatives for Metal Working Fluids—Ethanolamines", *J. Amer. Soc. Lubri. Engin.* 35: 137–144 (1979), the entire reference of which is incorporated herein by reference.

The antimicrobial composition formulations of the present invention are particularly attractive due to the low toxicity of their components when present in the amounts indicated. Furthermore, while prior known antimicrobial formulations appear to be effective at best in only about 42% of the commercially available metal-working fluids, the formulations of the present invention are more universally effective.

While the invention has been explained in relation to certain illustrative embodiments of it, it is understood that many modifications and substitutions may be made in any of the specific embodiments within the scope of the appended claims which are intended also to cover equivalents of them. Furthermore, the invention may comprise, consist or consist essentially of the herein recited steps and materials.

What is claimed is:

1. A method of inhibiting microbial growth in an aqueous fluid medium susceptible to such growth which comprises adding to said medium an antimicrobially effective amount of n-hexyl ethanolamine.

2. The method of claim 1 wherein the weight amount of n-hexyl ethanolamine ranges from about 1000 to 4000 parts per million parts by weight of the aqueous medium.

3. A metalworking coolant fluid comprising:
one part by volume of a lubricant including fatty or petroleum oils, soaps, or synthetic based petroleum oils, and about 20 to about 40 parts by volume of water containing an antimicrobially effective amount of n-hexyl ethanolamine.

4. The metalworking coolant of claim 3 wherein the lubricant comprises a water miscible oil.

5. The metalworking coolant fluid of claim 3 wherein the amount of n-hexyl ethanolamine ranges from about 1000 to 4000 parts per million by weight of the combined lubricant and water.

6. The method of claim 1 wherein the aqueous fluid medium is a metalworking coolant fluid comprising a lubricant including fatty or petroleum oils, soaps, or synthetic based petroleum oils, and water.

7. The method of claim 6 wherein the lubricant comprises a water miscible oil.

* * * * *